(12) United States Patent
Fukuda et al.

(10) Patent No.: US 7,417,162 B2
(45) Date of Patent: *Aug. 26, 2008

(54) OILY INGREDIENT FOR COSMETIC PREPARATION AND COSMETIC PREPARATION

(75) Inventors: Yukitoshi Fukuda, Yokkaichi (JP); Ikuo Shimizu, Yokkaichi (JP); Katsuhiro Ito, Yokkaichi (JP); Kazuyasu Osada, Yokkaichi (JP); Tomoya Takahashi, Chiyoda-ku (JP)

(73) Assignee: Kyowa Yuka Co., Ltd., Tokyo (JP)

( * ) Notice: Subject to any disclaimer, the term of this patent is extended or adjusted under 35 U.S.C. 154(b) by 767 days.

This patent is subject to a terminal disclaimer.

(21) Appl. No.: 10/487,360

(22) PCT Filed: Aug. 21, 2002

(86) PCT No.: PCT/JP02/08426

§ 371 (c)(1),
(2), (4) Date: Feb. 20, 2004

(87) PCT Pub. No.: WO03/015735

PCT Pub. Date: Feb. 27, 2003

(65) Prior Publication Data

US 2004/0219178 A1 Nov. 4, 2004

(30) Foreign Application Priority Data

Aug. 21, 2001 (JP) ............... 2001-249780

(51) Int. Cl.
  A61Q 17/04 (2006.01)
  C07C 69/34 (2006.01)
  C07C 67/36 (2006.01)

(52) U.S. Cl. ................ 560/190; 424/59; 514/63

(58) Field of Classification Search ......... 424/401, 424/59; 508/465; 514/63; 560/190–204
See application file for complete search history.

(56) References Cited

U.S. PATENT DOCUMENTS

| 6,576,678 B1 | 6/2003 | Bruening et al. ............ 516/22 |
| 2005/0130850 A1* | 6/2005 | Fukuda et al. ............ 508/110 |

FOREIGN PATENT DOCUMENTS

| EP | 0 791 353 | 8/1997 |
| JP | 07/14847 | 2/1995 |
| JP | 09-263524 | 10/1997 |
| WO | WO 99/67016 | 12/1999 |

OTHER PUBLICATIONS

Hayen, et al., 1,3-Stereoinduction in Radical Reactions: Radical Additions to Dialkyl 2-Alkyl-4-methyleneglutarates, *J. Am. Chem. Soc.*, vol. 122, No. 50 (2000), pp. 12458-12468.
Ozegowski, et al., "The Enzyme-Catalyzed Sequential Esterification of . . . ", *Liebigs Ann. Chem.* (1994), pp. 215-217.
Fukuoka, et al., "Activation of Mixed Carboxylic α-Bromotoluoyl . . . ", *Tetrahedron Letters*, vol. 28, No. 40 (1987), pp. 4711-4712.
Rousseau, et al., "Reaction of Silyketene Acetals with Acryloyl and . . . ", *Tetrahedron Letters*, vol. 26, No. 35 (1985), pp. 4191-4194.
Wallace, et al., "1,5-Bis(Trimethysiloxy)-1, 5-Dimethoxy-1, 4-Pentadienes", *Tetrahedron*, vol. 39, No. 6 (1983), pp. 847-853.
Halfpenny, et al., "Conformational Effects in Compounds with 6-Membered Rings-X", *Tetrahedron*, vol. 32 (1976), pp. 1873-1879.
Chemical Abstracts (1961), vol. 55, the Abstract No. 371h.
Mori, et al., "Synthesis of the Three Stereoisomers of Auxin-Glutaric Acid to Confirm the . . . ", *Liebigs Ann. Chem.* (1991), pp. 775-781.
Saiz, et al., "Conformational Characteristics of Phenyl and Chlorophenyl . . . ", *Macromolecules* (1989), vol. 22, No. 3, pp. 1330-1334.
Dinz-Calleja, et a., "Relaxation Studies on Model Compounds of Cyclohexyl-Based Polyacrylates", *J. Phys. Chem.*, vol. 96, No. 2 (1992), pp. 931-936.
Ikeda, et al., "Organometallic Compound With Lewis Base . . . ", *Tetrahedron*, vol. 30 (1974), pp. 2217-2225.
Naemura, et al., "Synthesis of Novel Crown Ether Incorporating . . . ", *Chemistry Letters* (1985), No. 11, pp. 1651-1654.
Chemistry Express, vol. 8, No. 9 (1993), pp. 721-724.
Chemical Abstract, vol. 51 (1957), the abstract No. 317f.

* cited by examiner

*Primary Examiner*—Johann Richter
*Assistant Examiner*—Konata M George
(74) *Attorney, Agent, or Firm*—Fitzpatrick, Cella, Harper & Scinto

(57) ABSTRACT

The present invention provides oils for cosmetics comprising a dibasic acid diester represented by general formula (I)

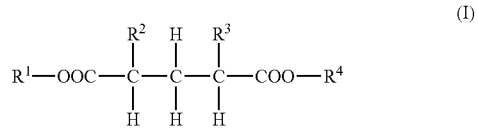

(wherein $R^1$, $R^2$, $R^3$ and $R^4$, which are the same or different, each represent lower alkyl)
and excellent in solubility of a long-wave ultraviolet light absorber or the like, and so forth.

16 Claims, No Drawings

OILY INGREDIENT FOR COSMETIC PREPARATION AND COSMETIC PREPARATION

TECHNICAL FIELD

The present invention relates to oils for cosmetics excellent in solubility of a long-wave ultraviolet light (UV-A: 320 to 400 nm) absorber and cosmetics comprising the oil for cosmetics.

BACKGROUND ART

Among components added to skin care products, ultraviolet light absorbers are divided into a UV-A absorber and a medium-wave ultraviolet light (UV-B: 280 to 320 nm) absorber.

Recently, it has been found that UV-A enhances pigmentation such as blemish or freckle and dermatopathy due to UV-B, and the development of a UV-A absorber has been regarded as important. Examples of the currently known UV-A absorber include benzophenone derivatives, benzotriazole derivatives, dibenzoylmethane derivatives (4-(tert-butyl)-4'-methoxydibenzoylmethane and the like) (Japanese Published Examined Patent Application No.86-16258) and the like. Meanwhile, oils currently used for cosmetics have a problem that they are poor in solubility of the UV-A absorber and cannot make cosmetics contain a sufficient amount of the UV-A absorber.

As oils for cosmetics excellent in solubility of a UV-A absorber, esters of a carboxylic acid or dibasic acid having from 4 to 18 carbon atoms and an alcohol having from 2 to 18 carbon atoms which have a total carbon number of 12 or more (isopropylmyristate, cetyloctanoate, 2-ethylhexylpalmitate, 2-ethylhexyl succinate and the like) are disclosed (Japanese Published Unexamined Patent Application No.97-263524). However, the development of oils for cosmetics having better solubility of a UV-A absorber has been in demand.

Moreover, cosmetics using 2-ethylhexyl succinate and the like have problems in that they do not show good emulsifiability based on phospholipid, sorbitan-type surfactants and the like, that they are insufficient in moist feeling, smoothness and the like when used as creams or the like and that they are insufficient in combing, moist feeling and the like when used as hair care products. Thus, they are unsatisfactory in practical use.

DISCLOSURE OF THE INVENTION

An object of the invention is to provide oils for cosmetics comprising a dibasic acid diester and excellent in solubility of a UV-A absorber, and cosmetics comprising the oil for cosmetics and a UV-A absorber.

The invention provides the following [1] to [6].

[1] Oil for cosmetics comprising a dibasic acid diester represented by general formula (I)

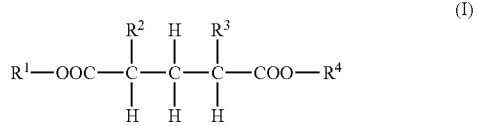

(wherein $R^1$, $R^2$, $R^3$ and $R^4$, which are the same or different, each represent lower alkyl, lower alkenyl, lower alkynyl, cycloalkyl, aryl or aralkyl).

[2] Cosmetics comprising the oil for cosmetics according to the above-mentioned [1].

[3] Cosmetics comprising the oil for cosmetics according to the above-mentioned [1] and a UV-A absorber.

[4] The cosmetics according to the above-mentioned [3], wherein the UV-A absorber is a dibenzoylmethane derivative.

[5] A dibasic acid diester represented by general formula (Ia)

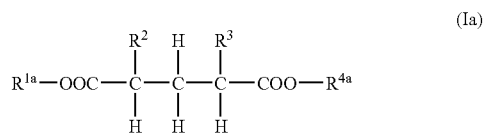

(wherein $R^2$ and $R^3$ are as defined above respectively, and $R^{1a}$ and $R^{4a}$, which are the same or different, each represent lower alkyl, lower alkenyl, lower alkynyl, cycloalkyl, aryl or aralkyl, provided that they are not ethyl at the same time).

[6] The dibasic acid diester wherein $R^2$ and $R^3$ are each lower alkyl.

The dibasic acid diester represented by general formula [I] is sometimes referred to as compound (I).

In the definitions of the respective groups in general formulae (I) and (Ia), the lower alkyl includes straight chain or branched alkyl having 1 to 8 carbon atom(s). Specific examples thereof include methyl, ethyl, propyl, isopropyl, butyl, isobutyl, sec-butyl, tert-butyl, pentyl, isoamyl, neopentyl, hexyl, heptyl, octyl, isooctyl, 2-ethylhexyl and the like. Among these, methyl, ethyl, propyl or isopropyl is preferable.

The lower-alkenyl includes straight chain or branched alkenyl having 2 to 8 carbon atoms. Specific examples thereof include vinyl, allyl, 1-propenyl, methacryl, crotyl, 1-butenyl, 3-butenyl, 2-pentenyl, 4-pentenyl, 2-hexenyl, 5-hexenyl, heptenyl, octenyl and the like.

The lower alkynyl includes straight chain or branched alkynyl having 2 to 8 carbon atoms. Specific examples thereof include ethynyl, propynyl, butynyl, pentynyl, hexynyl, heptynyl, octynyl and the like.

The cycloalkyl includes cycloalkyl having 3 to 8 carbon atoms and specific examples thereof include cyclopropyl, cyclobutyl, cyclopentyl, cyclohexyl, cycloheptyl, cyclooctyl and the like.

The aryl and the aryl moiety of the aralkyl include aryl having 6 to 14 carbon atoms and specific examples thereof include phenyl, naphthyl, anthryl and the like. An alkylene moiety of the aralkyl has the same meaning as a group in which one hydrogen atom is removed from the above-mentioned definition of the lower alkyl.

Among the dibasic acid diesters represented-by general formula (I), those wherein $R^2$ and $R^3$ are both ethyl are preferable, and those wherein $R^2$ and $R^3$ are both ethyl and $R^1$ and $R^4$ are both methyl are more preferable. Among the dibasic acid diesters represented by general formula (Ia), those wherein $R^2$ and $R^3$ are both lower alkyl are preferable, and those wherein $R^2$ and $R^3$ are both ethyl are more preferable.

Compound (I) can be synthesized by a known method for the synthesis of esters. For example, compound (I) can be obtained by reacting a corresponding dibasic acid with 1 to 10 equivalents, preferably 1 to 2 equivalents (molar ratio) of an aliphatic alcohol at from 50 to 150° C., in the presence of an azeotropic agent if necessary and in the presence of a catalytic amount to 0.5 equivalent (molar-ratio) of an acid catalyst such as p-toluenesulfonic acid. Examples of the azeotropic agent include toluene, benzene and the like, and these are generally used in an amount of from 0.5 to 100 equivalents (weight ratio) based on a dibasic acid.

The dibasic acid as a starting material can be produced by treating a corresponding diol in the presence of 1 to 5 equivalents (molar ratio) of a base such as sodium hydroxide or potassium hydroxide preferably at 200 to 320° C. in a manner similar to a known method [Yukagaku, vol. 19, No. 12, p. 1087 (1970), Japanese Published Unexamined Patent Application No.94-72948 or the like]. Also, in the treatment, a reaction solvent, for example, an ether solvent such as dibenzyl ether or a hydrocarbon solvent such as liquid paraffin (having 10 to 16 carbon atoms) may be used.

In the oil for cosmetics of the present invention, compound (I) is contained in an amount of, preferably 10% by weight or more, more preferably 30% by weight or more based on the total weight. The oil for cosmetics of the present invention may contain, as a component other than compound (I), an oil component. Examples of the oil component include ester-type oil, hydrocarbon-type oil, silicone-type oil, fluorine-comprising oil, animal and plant oils, and the like.

Examples of the ester-type oil include esters such as glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, glyceryl monostearate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, glyceryl tri(capryl·caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, stearyl 2-ethylhexanoate, cetostearyl 2-ethylhexanoate (mixture of cetyl 2-ethylhexanoate and stearyl 2-ethylhexanoate), glyceryl di-p-methoxycinnamic acid-mono-2-ethylhexanoate, hexyl isostearate, ethylene glycol dioctanoate, ethylene glycol dioleate, propylene glycol dicaprate, propylene glycol di-(capryl·caprate), propylene glycol dicaprylate, neopentylglycol dicaprate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isostearyl isostearate, octyldecyl, isostearate, polyglycerol oleate, polyglycerol isostearate, triisocetyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyloxystearate, stearyl 12-stearoyloxystearate and isostearyl 12-stearoyloxystearate.

Examples of the hydrocarbon-type oil include squalane, liquid paraffin, α-olefin oligomer, isoparaffin, ceresine, paraffin, liquid isoparaffin, polybutene, microcrystalline wax, vaseline and the like.

Examples of the silicone-type oil include polymethylsilicone, methylphenylsilicone, methylcyclopolysiloxane, octamethylpolysiloxane, decamethylpolysiloxane, dodecamethylcyclosiloxane, a dimethylsiloxane.methylcetyloxysiloxane copolymer, a dimethylsiloxane.methyl- stearoyloxysiloxane copolymer, alkyl-modified silicone oil, amino-modified silicone oil and the like.

Examples of the fluorine-comprising oil include perfluoropolyether and the like.

Examples of the animal and plant oils include animal and plant oils such as avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cotton seed oil, coconut oil, kukui nut oil, wheat embryo oil, rice embryo oil, shea butter, evening primrose oil, macadamia nut oil, meadow foam oil, yolk oil, tallow, horse oil, mink oil, orange roughy oil, jojoba oil and the like.

The oil component is comprised in the oil for cosmetics of the present invention in an amount of, preferably 70% by weight or less, more preferably 60% by weight or less.

Since compound (I) is excellent in solubility of a UV-A absorber, a large amount of the UV-A absorber can be dissolved in the oil for cosmetics of the present invention [from this aspect, compound (I) can also be used as a solubilizer of the UV-A absorber].

The cosmetics of the present invention contains the oil for cosmetics comprising compound (I). The content of the oil for cosmetics is preferably 0.1 to 60% by weight, more preferably 1 to 50% by weight, further preferably from 5 to 40% by weight based on the total weight of the cosmetics.

When the cosmetics of the present invention contains the UV-A absorber, the UV-A absorber is comprised in compound (I) in an amount of, preferably 0.5 to 80% by weight, more preferably from 1 to 70% by weight.

Preferable examples of the UV-A absorber include benzophenone derivatives such as 2-hydroxy-4-methoxybenzophenone, 2-hydroxy-4-methoxybenzophenonesulfonic acid or salts thereof, 2,2'-dihydroxy-4-methoxybenzophenone, disodium 2,2'-dihydroxy-4-methoxybenzophenonedisulphate 2,2'-dihydroxybenzophenone, and 2,2'-4,4'-tetrahydroxybenzophenone, benzotriazole derivatives such as 2-(2-hydroxy-5-methylphenyl)benzotriazole, dibenzoylmethane derivatives such as 4-(tert-butyl)-4'-methoxydibenzoylmethane. Among these, dibenzoylmethane derivatives are preferably used, 4-(tert-butyl)-4'-methoxydibenzoylmethane is more preferably used.

The cosmetics of the present invention may contain, as required, other components such as a humectant, an emollient, a surfactant, an organic or inorganic pigment, an organic powder, a UV-B absorber, an antiseptic, a disinfectant, an antioxidant, a plant extract, a pH modifier, a perfume, an emulsion stabilizer and purified water.

Examples of the humectant include a water-soluble low-molecular humectant, a fat-soluble low-molecular humectant, a water-soluble polymer, a fat-soluble polymer and the like.

Examples of the water-soluble low-molecular humectant include serine, glutamine, sorbitol, mannitol, glycerol, propylene glycol, 1,3-butylene glycol, ethylene glycol, polyethylene glycol (degree of polymerization n=2 or more), polypropylene glycol (degree of polymerization n=2 or more), polyglycerol (degree of polymerization n=2 or more), dynamite glycerol, lactic acid, lactate and the like.

Examples of the fat-soluble low-molecular humectant include cholesterol, cholesterol ester and the like.

Examples of the water-soluble polymer include carboxyvinyl polymer, polyaspartic acid salt, tragacanth, xanthane gum, methylcellulose, hydroxymethylcellulose, hydroxyethylcellulose, hydroxypropylcellulose, carboxymethylcellulose, water-soluble chitin, chitosan, dextrin and the like.

Examples of the fat-soluble polymer include a polyvinylpyrrolidone.eicosene copolymer, a polyvinylpyrrolidone.hexadecene copolymer, nitrocellulose, dextrin fatty acid ester, polymeric silicone and the like.

Examples of the emollient include cholesteryl long-chain-acylglutamate, cholesteryl hydroxystearate, 12-hydroxystearic acid, stearic acid, rosic acid, lanolin fatty acid cholesteryl ester and the like.

Examples of the surfactant include a nonionic surfactant, an anionic surfactant, a cationic surfactant, an ampholytic surfactant and the like.

Examples of the nonionic surfactant include a propylene glycol fatty acid ester, a glycerol fatty acid ester, a polyglycerol fatty acid ester, a sorbitan fatty acid ester, a POE (polyoxyethylene) sorbitan fatty acid ester, a POE sorbitol fatty acid ester, a POE glycerol fatty acid ester, a POE alkyl ether, a POE fatty acid ester, POE hardened castor oil, POE castor oil, a POE.POP (polyoxypropylene) copolymer, a POE.POP alkyl ether, a polyether-modified silicone, an alkanolamide laurate, an alkylamine oxide, hydrogenated soybean phospholipid and the like.

Examples of the anionic surfactant include a fatty acid soap, an α-acyl sulfonate, an alkyl sulfonate, an alkylallyl sulfonate, an alkylnaphthalene sulfonate, an alkyl sulfate, a POE alkyl ether sulfate, an alkylamide sulfate, an alkyl phosphate, a POE alkyl phosphate, an alkylamide phosphate, an acylalkyl taurate, an N-acyl amino acid salt, a POE alkyl ether carboxylate, an alkyl sulfosuccinate, a sodium alkylsulfoacetate, an acylated collagen hydrolyzate peptide salt, a perfluoroalkyl phosphate and the like.

Examples of the cationic surfactant include an alkyltrimethylammonium chloride, a stearyltrimethylammonium chloride, cetostearyltrimethylammonium chloride (mixture of stearyltrimethylammonium chloride and cetyltrimethylammonium chloride), stearyltrimethylammonium bromide, distearyldimethylammonium chloride, stearyldimethylbenzylammonium chloride, behenyltrimethylammonium bromide, benzalkonium chloride, diethylaminoethylamide stearate, dimethylaminopropylamide stearate, lanolin derivative quaternary ammonium salt and the like.

Examples of the ampholytic surfactant include ampholytic surfantants such as carboxybetaine-type, amidobetaine-type, sulfobetaine-type, hydroxysulfobetaine-type, amidosulfobetaine-type, phosphobetaine-type, aminocarboxylic acid salt-type, imidazoline derivative-type and amidoamine-type.

Examples of the organic or inorganic pigment include inorganic pigments such as silicic acid, silicic anhydride, magnesium silicate, talc, sericite, mica, kaolin, red oxide, clay, bentonite, titanium-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine and carbon black; organic pigments such as a polyamide, a polyester, polypropylene, polystyrene, polyurethane, a vinyl resin, a urea resin, a phenolic resin, a fluororesin, a silicon resin, an acrylic resin, a melamine resin, an epoxy resin, a polycarbonate resin, a divinylbenzene.styrene copolymer, a silk powder, cellulose, CI pigment yellow and CI pigment orange; and composite pigments of these inorganic pigments and organic pigments.

Examples of the organic powder include metallic soaps such as calcium stearate; alkylphosphate polyvalent metallic salts such as zinc sodium cetylphosphate, zinc laurylphosphate and calcium laurylphosphate; acylamino acid polyvalent metal salts such as N-lauroyl-β-alanine calcium salt, N-lauroyl-β-alanine zinc salt and N-lauroylglycine calcium salt; amidosulfonic acid polyvalent metal salts such as N-lauroyltauline calcium salt and N-palmitoyltaurine calcium salt; N-acyl basic amino acid salt such as Nε-lauroyllysine, Nε-palmitoyllysine, Nα-palmitoylornitine, Nα-lauroylarginine and Nα-hardened tallow fatty acid acylarginine; N-acyl polypeptides such as N-lauroylglycylglycine; α-amino fatty acids such as α-aminocaprylic acid and α-aminolauric acid; polyethylene, polypropylene, nylon, polymethyl methacrylate, polystyrene, a divinylbenzene.styrene copolymer, ethylene tetrafluoride and the like.

Examples of the WV-B absorber include p-aminobenzoic acid, ethyl p-aminobenzoate, amyl p-aminobenzoate, octyl p-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl p-methoxycinnamate, octyl p-methoxycinnamate, glyceryl di-p-methoxycinnamic acid mono-2-ethylhexanoate, isopropyl p-methoxycinnamate, a diisopropyl.diisopropyl cinnamate mixture, urocanic acid, ethyl urocanate and the like.

Examples of the antiseptic include paraben, methyl paraben, propyl paraben and the like.

Examples of the disinfectant include hinokithiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, light-sensitive pigment No. 301 (manufactured by Nippon Kanko Shikiso Kenkyusho) mononitroguaiacol sodium, undecylenic acid and the like.

Examples of the antioxidant include butylhydroxyanisol, propyl gallate, erythorbic acid and the like.

Examples of the plant extract include an extract of *Angelica keiskei*, an extract of avocado, an extract of *hydrangea* leaves, an extract of *althaea*, an extract of *arnica*, an extract of aloe, an extract of apricot, an extract of apricot kernel, an extract of ginkgo, an extract of fennel, an extract of turmeric, an extract of oolong tea, an extract of rose fruits, an extract of *echinacea* leaf, an extract of *scutellaria* root, an extract of *phellodendron* bark, an extract of Japanese *coptis*, an extract of wheat, an extract of *hypericum*, an extract of *lamium*, an extract of *nasturtium*, an extract of orange, an extract of chamomile, an extract of carrot, an extract of *artemisia*, an extract of licorice, an extract of carcade, an extract of *Ryracantha fortuneana*, an extract of *Pyrantha Fortuneana* Fruit, an extract of kiwi, an extract of *cinchona*, an extract of cucumber, an extract of *gardenia*, an extract of *Sasa albomarginata*, an extract of *sophora*, an extract of walnut, an extract of grapefruit, an extract of *clematis*, an extract of *chlorella*, an extract of mulberry, an extract of *gentian*, an extract of black tea, an extract of comfrey, collagen, an extract of cowberry, an extract of *asiasarum* root, an extract of *bupleurum* root, an extract solution of Umbical Cord, an extract of *melilotus*, an extract of *salvia*, an extract of soapwort, an extract of bamboo grass, an extract of hawthorn, an extract of Japanese pepper, an extract of shiitake, an extract of *Rehmannia glutinosa*, an extract of *lithospermum* root, an extract of labiate, an extract of Japanese linden, an extract of *Filipendula multijuga*, an extract of *Paeonia lactiflora*, an extract of Japanese *iris* root, an extract of white birch, an extract of field horsetail, an extract of English ivy, an extract of *Crataegus monogyna*, an extract of *Sambucus nigra*, an extract of *Achillea millefolium*, an extract of lemon balm, an extract of sage, an extract of common mallow, an extract of *cnidium rhizome*, an extract of *Swertia japonica*, an extract of soybean, an extract of jujube, an extract of thyme, an extract of tea plant, an extract of clove, an extract of cogon, an extract of *citrus unshiu* peel, an extract of Japanese *angelica* root, an extract of *calendula*, an extract of peach kernel, an extract of bitter orange peel, an extract of *Houttuynia cordata*, an extract of tomato, an extract of *ginseng*, an extract of garlic, an extract of wild rose, an extract of hibiscus, an extract of ophiopogon tuber, an extract of parsley, beeswax, an extract of *hamamelis*, an extract of Pellitory, an extract of *Plectranthus japonicus*, bisabolol, an extract of loquat, an extract of *Tussilago farfara*, an extract of butterbur flower, an extract of *Pachyma hoelen*, an extract of butcher's bloom, an extract of grape, propolis, an extract of sponge cucumber, an extract of safflower, an extract of pepper mint, an extract of linden, an extract of *Paeonia suffruticosa*, an extract of hop, an extract of pine, an extract of horse chestnut, an extract of lysichiton, an extract of soapberry, an extract of melissa, an extract of peach, an extract of cornflower, an extract of eucalyptus, an extract of saxifrage, an extract of citron, an extract of coix seed, an extract of mugwort, an extract of lavender, an extract of apple, an extract of lettuce, an extract of lemon, an extract of Chinese milk vetch, an extract of rose, an extract of rosemary, an extract of Roman chamomile, and the like.

Examples of the pH adjustor include citric acid, sodium citrate, malic acid, sodium malate, fumaric acid, sodium fumarate, succinic acid, sodium succinate, sodium hydroxide, disodium hydrogenphosphate and the like.

Examples of the perfume include jasmine oil, clove oil, peppermint oil, vanilla, rose oil, bergamot oil, lavender oil, musk, ambergris, vanillin and the like.

Examples of the emulsion stabilizer include stearyl alcohol, cetyl alcohol and the like.

Incidentally, the other components are not limited thereto.

All of the foregoing components can be incorporated unless the object and the effects of the invention are impaired. They are incorporated in an amount of, preferably 0.01 to 5% by weight, more preferably 0.01 to 3% by weight based on the total weight.

The cosmetics of the present invention can take the form of, for example, a solution, an emulsion or a pasty mixture.

The mode of the cosmetics is not particularly limited. Examples thereof include an emulsion, a cream, a cosmetic lotion, a foundation, a lotion, a beauty liquid and the like.

Specific examples of the cosmetics of the invention include an emulsion, a cosmetic lotion, an anti-sunburn cream, anti-sunburn oil, a lipstick, a hair care product and the like.

The cosmetics of the present invention shows good emulsifiability with phospholipids (hydrogenated soybean phospholipid, purified yolk lecithin, soybean phospholipid, soybean lysophospholipid and the like) and sorbitan-type surfactants [sorbitan monolaurate, sorbitan monopalmitate, sorbitan monostearate, sorbitan monoisostearate, sorbitan monooleate, sorbitan tristearate, sorbitan trioleate, polyoxyethylene (20) sorbitan monolaurate, polyoxyethylene (20) sorbitan monopalmitate, polyoxyethylene (6) sorbitan monostearate, polyoxyethylene (20) sorbitan monoisostearate, polyoxyethylene (6) sorbitan monooleate, polyoxyethylene (20) sorbitan monooleate, polyoxyethylene (20) sorbitan tristearate, polyoxyethylene (20) trioleate and the like].

When the cosmetics of the present invention is used in the mode of a cream or the like, the cream or the like has a good moist feeling, good smoothness and the like.

When the cosmetics of the present invention is used as a hair care product or the like, the hair care product has good combing, a good moist feeling and the like.

The cosmetics of the present invention can be obtained by preparing compound (I), preferably the UV-A absorber, and the above-mentioned components to be added as required according to a known method, for example, a method described in, "Keihi Tekiyo Seizai Kaihatsu Manyuaru (Manual of Development of Preparations for Subcutaneous Application)", supervised by Matsumoto Mitsuo, 1st Ed. (Seishi Shoin, published 1985).

The cosmetics comprising the UV-A absorber in the present invention is cosmetics which can effectively control sunburn or the like caused by UV-A.

BEST MODE FOR CARRYING OUT THE INVENTION

Preparation Examples of the cosmetics of the present invention are described below.

PREPARATION EXAMPLE 1

Preparation of a Water/Oil Emulsion

A water/oil emulsion is formed by mixing components in the following proportions (% means % by weight).

| Oily layer; | |
| --- | --- |
| Glyceryl di-p-methoxycinnamic acid-mono-2-ethylhexanoate | 1.0% |
| 4-(tert-butyl)-4'-methoxydibenzoylmethane | 1.0% |
| 2-hydroxy-4-methoxybenzophenone | 1.0% |
| cetyl alcohol | 1.0% |
| squalane | 20.0% |
| vaseline | 1.0% |
| dibutyl 2,4-diethylglutarate | 30.0% |
| jojoba oil | 1.0% |
| glyceryl monostearate | 3.0% |
| magnesium silicate | 2.0% |
| distearyldimethylammonium chloride | 1.0% |
| paraben | 0.2% |
| Aqueous layer; | |
| dynamite glycerol | 3.0% |
| extract of melilotus | 0.5% |
| deionized water | balance |

PREPARATION EXAMPLE 2

Preparation of an Oil/Water Emulsion

An oil/water emulsion is formed by mixing components in the following proportions (% means % by weight).

| Oily layer; | |
| --- | --- |
| glyceryl di-p-methoxycinnamic acid-mono-2-ethylhexanoate | 1.0% |
| 4-(tert-butyl)-4'-methoxydibenzoylmethane | 1.0% |
| 2-hydroxy-4-methoxybenzophenone | 1.0% |
| cetyl alcohol (emulsion stabilizer) | 1.0% |
| dibutyl diethylglutarate | 3.0% |
| squalane | 20.0% |
| vaseline | 1.0% |
| jojoba oil | 1.0% |
| glyceryl monostearate | 3.0% |
| paraben | 0.2% |
| Aqueous layer; | |
| dynamite glycerol | 3.0% |
| extract of melilotus | 0.5% |
| deionized water | balance |

REFERENCE EXAMPLE 1

Into a 1-liter nickel autoclave fitted with a reflux unit, a pressure control valve and an electrically-heated oven capable of controlling a temperature, 160.3 g of 2,4-diethyl-1,5-pentanediol (trade name: Kyowa Diol PD-9, manufactured by Kyowa Yuka K.K., purity 93.9%), 156.6 g of potassium hydroxide (purity 86%) and 102.2 g of a paraffin mixture having 12 carbon atoms (trade name: Kyowa Sol C1200-H, manufactured by Kyowa Yuka K.K.) were charged, and heat-stirred under 1 MPa. A hydrogen gas generated was measured with a gas meter to trace progression of the reaction. Generation of a gas was confirmed at approximately 230° C., and the reaction was further continued while maintaining the temperature at from 250 to 270° C. From the time when the temperature reached 250° C. to 3.5 hours later, 89.4 L of hydrogen was generated. The reaction was further continued for 30 minutes, during which 0.8 L of the hydrogen gas was generated. The amount of hydrogen generated coincided with the theoretical amount, and a reaction rate was 100%. After the reaction, a reaction solution comprising dipotassium 2,4-diethylglutarate was dissolved in water, sulfuric acid was further added, and a solid precipitated was collected by filtration to obtain crude 2,4-diethyl glutarate. This crude 2,4-diethyl glutarate was washed with water, purified by crystallization from n-hexane to obtain 142.5 g of 2,4-diethyl glutarate (white crystal). The purity of the resulting 2,4-diethyl glutarate was 98.3% (calculated from an acid value) (yield 79.1%).

The measurement data in the following Examples and Test Examples were obtained with the following measuring devices.

Mass spectrum (MS): M-80B mass analyzer (manufactured by Hitachi Ltd.)

Infrared spectrum (IR): FTS-40A (manufactured by Japan Bio-Rad)

Proton nuclear magnetic resonance spectrum ($^1$H-NMR): GSX-400 (400 MHz) (manufactured by JEOL Ltd.)

Electronic gravimeter SP-120L mode (manufactured by Millage Boeki K.K.)

Absorbance: U-3210 model automatic spectrophotometer (manufactured by Hitachi Ltd.)

EXAMPLE 1

Synthesis of diisobutyl 2,4-diethylglutarate (Compound 1)

Into a reaction flask, 2,4-diethylglutaric acid (94.74 g), isobutyl alcohol (74.87 g) and toluene (168.6 g) were charged into a reaction flask, and stirred well. Then, p-toluenesulfonic acid monohydrate (3.80 g) was added, and the mixture was refluxed for 7 hours. The reaction mixture was cooled to room temperature, neutralized with magnesium oxide, and washed with water. From the resulting reaction solution, the solvent was distilled off in vacuo by low boiling at 80° C. to obtain 143 g of compound 1 (yield: 93.8%). The physical properties of this compound were as follows.

$^1$H-NMR (CDCl$_3$, δppm); 3.86 (m, 4H), 2.31 (m, 2H), 1.93 (m, 2H), 1.60 (m, 6H), 0.95 (m, 18H) IR (cm$^{-1}$); 2974, 2952, 2889 (C—H), 1748 (C=O), 1467, 1383, 1253, 1166 (COOCH$_2$CH(CH$_3$)$_2$) MS (m/z); 301 (M$^+$) Density (kg/m$^3$); 922 (25° C.)

EXAMPLE 2

Synthesis of dibutyl 2,4-diethylglutarate (Compound 2)

Into a reaction flask, 2,4-diethylglutaric acid (94.71 g), n-butanol (74.20 g) and toluene (168.3 g) were charged, and stirred well. Then, p-toluenesulfonic acid monohydrate (3.80 g) was added, and the mixture was refluxed for 7 hours. The reaction mixture was cooled to room temperature, neutralized with a 4.8% by weight sodium hydroxide aqueous solution, and washed with water. From the reaction solution, the solvent was distilled off in vacuo by low boiling at 100° C. to obtain 111 g of compound 2 (yield: 73.4%). The physical properties of this compound were as follows.

$^1$H-NMR (CDCl$_3$, δppm); 4.07 (m, 4H), 2.29 (m, 2H), 1.94-1.36 (m, 14H), 0.88 (m, 12H) IR (cm$^{-1}$); 2973, 2947, 2888 (C—H), 1747 (C=O), 1465, 1391, 1261, 1221, 1164 (COO(CH$_2$)$_3$CH$_3$) MS (m/z); 301 (M$^+$) Density (kg/m$^3$); 929 (25° C.)

EXAMPLE 3

Synthesis of dimethyl 2,4-diethylglutarate (Compound 3)

Into a reaction flask, 2,4-diethylglutaric acid (94.11 g), methanol (64.00 g) and toluene (168.0 g) were charged, and stirred well. Then, p-toluenesulfonic acid monohydrate (3.86 g) was added, and the mixture was refluxed for 3.5 hours. The reaction mixture was cooled to room temperature, neutralized with a 4.8% by weight sodium hydroxide aqueous solution, and washed with water. From the reaction solution, the solvent was distilled off in vacuo by low boiling at 110° C. to obtain 29.9 g of compound 3 (yield: 27.4%). The physical properties of this compound were as follows.

$^1$H-NMR (CDCl$_3$, δppm); 3.67 (d, 6H, J=4.4 Hz), 2.30 (m, 2H), 1.96-1.59 (m, 6H), 0.88 (t, 6H, J=7.4 Hz) IR (cm$^{-1}$); 2971, 2890, 2854 (C—H), 1753 (C=O), 1459, 1441, 1260, 1221, 1167 (COOCH$_3$) MS (m/z); 217 (M$^+$) Density (kg/m$^3$); 992 (25° C.)

EXAMPLE 4

Synthesis of 2-ethylhexyl 2,4-diethylglutarate

Into a reaction flask, 2,4-diethylglutaric acid (92.50 g), 2-ethylhexanol (66.00 g) and toluene (157.3 g) were charged, and stirred well. Then, p-toluenesulfonic acid monohydrate (2.67 g) was added, and the mixture was refluxed for 5 hours. The reaction mixture was cooled to room temperature, neutralized with a 0.1% by weight sodium hydroxide aqueous solution, and washed with water. From the reaction solution, the solvent was distilled off in vacuo by low boiling at 135° C. to obtain 146 g of the compound 1 (yield: 98.4%). The physical properties of this compound were as follows.

$^1$H-NMR (CDCl$_3$, δppm); 3.98 (m, 4H), 2.32 (m, 2H), 1.94 (m, 1H), 1.75 (m, 1H), 1.59 (m, 4H), 1.28 (m, 18H), 0.95 (m, 18H) IR (cm$^{-1}$); 2972, 2942, 2887 (C—H), 1745 (C=O), 1465, 1388, 1261, 1163 (C—O) MS (m/z); 414 (M$^+$) Density (kg/m$^3$); 929 (25° C.)

COMPARATIVE EXAMPLE 1

Synthesis of di-2-ethylhexyl succinate (Comparative Compound 1)

Succinic acid (41.32 g), 2-ethylhexanol (92.34 g) and toluene (66.41 g) were charged into a reaction flask, and stirred well. Then, p-toluenesulfonic acid was added, and the mixture was refluxed for 3 hours. The reaction mixture was cooled to room temperature, neutralized with a 4.8% by weight sodium hydroxide aqueous solution, and washed with water. From the reaction solution, the solvent was distilled off in vacuo by low boiling while blowing water vapor at 90° C. to obtain 118 g of comparative compound 1 (yield: 97.46%).

TEST EXAMPLE 1

Test for Solubility of a UV-A Absorber

A test for solubility of a UV-A absorber [4-(tert-butyl)-4'-methoxybenzoylmethane (Palsol 1789, manufactured by Roche Vitamin Japan)] was performed using compound 3 and comparative compound 1 prepared in Example 3 and Comparative Example 1. Specifically, a supernatant of a solution obtained by dissolving the above-mentioned UV-A absorber in compound 3 or comparative compound 1 in a saturated state was diluted to 10 ppm with ethanol. Then, absorbance (A) of a peak observed near 350 nm was measured. Solubility was figured out from a value calculated by the following equation and a weight of a sample prepared. The measurement temperatures are at room temperature (approximately 250° C.) and 50° C.

Amount (mg) of UV-A absorber=A/113×20000

The results of the test for solubility are shown in Table 1.

TABLE 1

| | Solubility of a UV-A absorber [g/100 g] | |
|---|---|---|
| | room temperature (25° C.) | 50° C. |
| Compound 3 | 23.1 | 40.7 |
| Comparative compound 1 | 17.3 | 34.9 |

As seen from Table 1, it is found that compound 3 is, in comparison to comparative compound 1, excellent in solubility of the UV-A absorber [4-(tert-butyl)-4'-methoxydibenzoylmethane] and the oil for cosmetics of the present invention therefore contains the UV-A. absorber in a large amount in comparison to the oil for cosmetics comprising di-2-ethylhexyl succinate.

EXAMPLE 5

Preparation of a Cream

| (Fat-soluble components) | |
|---|---|
| hydrogenated soybean phospholipid | 3.2 g |
| dimethyl 2,4-diethylglutarate | 16 g |
| (Water-soluble components) | |
| purified water | 60.72 g |
| methyl p-oxybenzoate | 0.08 g |

(Method of Preparing a Cream)

(1) The foregoing fat-soluble components and water-soluble components were charged into different glass containers, and heated at 80° C. to be uniformly dissolved.

(2) The oil-soluble components were put in a stirrer. While the components were stirred at 2,000 rpm, ⅓ amount of the water-soluble components was added, and the mixture was further stirred at 4,000 rpm for 2 minutes.

(3) Subsequently, ⅔ amount of the water-soluble components was added, and the mixture was stirred at 4,000 rpm for 2 minutes.

(4) The mixture was cooled to 40° C. with running water.

(5) The next day, the thus-obtained cream was put in a thermostat of 40° C.

COMPARATIVE EXAMPLE 2

Preparation of a Cream

A cream was prepared in the same manner as in Example 5 except that dimethyl 2,4-diethylglutarate was replaced with di-2-ethylhexyl succinate.

EXAMPLE 3

Preparation of a Cream

A cream was prepared in the same manner as in Example 5 except that dimethyl 2,4-diethylglutarate was replaced with isopropyl palmitate.

TEST EXAMPLE 2

Test for Emulsifiability with Phospholipid

The creams prepared in Example 5 and Comparative Examples 2 and 3 were stored under a condition of 40° C., and storage stability was examined by a temperature acceleration test. The results are shown in Table 2.

TABLE 2

| | Example 5 | Comparative Example 2 | Comparative Example 3 |
|---|---|---|---|
| Before storage | not separated | separated | separated |
| Storage at 40° C. for 4 days | not separated | separated | separated |

As seen from Table 2, the cream obtained in Example 5 is stable in comparison to the creams obtained in Comparative Examples 2 and 3, showing the good emulsifiability.

That is, the cosmetics of the present invention shows the good emulsifiability with phospholipid.

EXAMPLE 6

Preparation of a Cream

| (Fat-soluble components) | |
|---|---|
| sorbitan monopalmitate | 3.2 g |
| dimethyl 2,4-diethylglutarate | 16 g |
| (Water-soluble components) | |
| purified water | 60.72 g |
| methyl p-oxybenzoate | 0.08 g |

A cream was prepared in the same manner as in Example 5 except that the fat-soluble components and the water-soluble components were changed as mentioned above.

COMPARATIVE EXAMPLE 4

Preparation of a Cream

A cream was prepared in the same manner as in Example 6 except that dimethyl 2,4-diethylglutarate was replaced with di-2-ethylhexyl succinate.

COMPARATIVE EXAMPLE 5

Preparation of a Cream

A cream was prepared in the same manner as in Example 6 except that dimethyl 2,4-diethylglutarate was replaced with isopropyl palmitate.

TEXT EXAMPLE 3

Test for Emulsifiability with Sorbitan Monopalmitate

The creams prepared in Example 6 and Comparative Examples 4 and 5 were stored under a condition of 40° C., and storage stability was examined by a temperature acceleration test. The results were shown in Table 3.

TABLE 3

|  | Example 6 | Comparative Example 4 | Comparative Example 5 |
|---|---|---|---|
| Before storage | Not separated | separated | separated |
| Storage at 40° C. for 4 days | Not separated | separated | separated |

As seen from Table 2, the cream obtained in Example 6 is stable in comparison to the creams obtained in Comparative Examples 4 and 5, showing the good emulsifiability.

EXAMPLE 7

Preparation of a Cream

| (Fat-soluble components) | |
|---|---|
| polyoxyethylene (20) sorbitan monostearate | 3.2 g |
| dimethyl 2,4-diethylglutarate | 16 g |
| (Water-soluble components) | |
| purified water | 60.72 g |
| methyl p-oxybenzoate | 0.08 g |

A cream was prepared in the same manner as in Example 5 except that the fat-soluble components and the water-soluble components were changed as mentioned above.

COMPARATIVE EXAMPLE 6

Preparation of a Cream

A cream was prepared in the same manner as in Example 7 except that dimethyl 2,4-diethylglutarate was replaced with di-2-ethylhexyl succinate.

COMPARATIVE EXAMPLE 7

Preparation of a Cream

A cream was prepared in the same manner as in Example 7 except that dimethyl 2,4-diethylglutarate was replaced with isopropyl palmitate.

TEST EXAMPLE 4

Test for emulsifiability with polyoxyethylene (20) sorbitan monostearate

The creams prepared in Example 7 and Comparative Examples 6 and 7 were stored under a condition of 40° C., and storage stability was examined by a temperature acceleration test. The results are shown in Table 4.

TABLE 4

|  | Example 7 | Comparative Example 6 | Comparative Example 7 |
|---|---|---|---|
| Before storage | Not separated | separated | separated |
| Storage at 40° C. for 4 days | Not separated | separated | separated |

As seen from Table 4, the cream obtained in Example 7 is stable in comparison to the creams obtained in Comparative Examples 6 and 7, showing the good emulsifiability.

That is, Tables 3 and 4 reveal that the cosmetics of the present invention have the good emulsifiability with the sorbitan-type surfactants.

EXAMPLE 8

Preparation of a Cream

| (Fat-soluble components) | |
|---|---|
| dimethyl 2,4-diethylglutarate | 8 g |
| glycerol di-p-methoxycinnamic acid mono-2-ethylhexanoate | 2 g |
| butylmethoxybenzoylmethane | 2 g |
| squalane | 16 g |
| camellia oil | 8 g |
| cetanol | 4 g |
| polyoxyethylene (20) cetyl ether | 2 g |
| glycerol monostearate | 4 g |
| sorbitan monopalmitate | 4 g |
| isopropyl p-oxybenzoate | 0.2 g |
| (Water-soluble components) | |
| purified water | 123.4 g |
| methyl p-oxybenzoate | 0.4 g |
| 1,3-butylene glycol | 6 g |
| (Polymer components) | |
| carboxyvinyl polymer | 0.1 g |
| purified water | 19.89 g |
| methyl p-oxybenzoate | 0.01 g |
| sodium hydroxide | suitable amount |

(Method of Preparing a Cream)

(1) The fat-soluble components and the water-soluble components were charged into different glass containers, and heated at 80° C. to be uniformly dissolved.

(2) The oil-soluble components were put in a stirrer. While the components were stirred at 2,000 rpm, ⅓ amount of the water-soluble components was added, and the mixture was further stirred at 4,000 rpm for 2 minutes.

(3) Subsequently, ⅔ amount of the water-soluble components was added, and the mixture was stirred at 4,000 rpm for 2 minutes.

(4) Further, the polymer components uniformly dissolved were added, and the mixture was stirred at 4,000 rpm for 2 minutes.

(5) The resulting mixture was cooled to 40° C. with running water.

EXAMPLE 9

Preparation of a Cream

A cream was prepared in the same manner as in Example 8 except that dimethyl 2,4-diethylglutarate was replaced with dibutyl 2,4-diethylglutarate.

EXAMPLE 10

Preparation of a Cream

A cream was prepared in the same manner as in Example 8 except that dimethyl 2,4-diethylglutarate was replaced with di-2-ethylhexyl 2,4-diethylglutarate.

COMPARATIVE EXAMPLE 8

Preparation of a Cream

A cream was prepared in the same manner as in Example 8 except that dimethyl 2,4-diethylglutarate was replaced with di-2-ethylhexyl succinate.

COMPARATIVE EXAMPLE 9

Preparation of a Cream

A cream was prepared in the same manner as in Example 8 except that dimethyl 2,4-diethylglutarate was replaced with isopropyl palmitate.

TEST EXAMPLE 5

Organoleptic Evaluation of a Cream

Woman volunteers who were from 24 to 40 years old and divided into groups each consisting of five women used the creams prepared in Examples 8 to 10 and Comparative Examples 8 and 9 twice a day for 2 weeks, and the organoleptic evaluation was performed. The evaluation was performed through score evaluation of five grades 1 to 5 (5: very good, 4: good, 3: average, 2: bad, 1: very bad) with respect to two items, a moist feeling and smoothness. The results are shown in Table 5.

TABLE 5

|  | Example 8 | Example 9 | Example 10 | Comparative Example 8 | Comparative Example 8 |
|---|---|---|---|---|---|
| Moist feeling | 4.2 | 4.0 | 4.6 | 3.8 | 3.4 |
| Smoothness | 4.8 | 4.2 | 3.8 | 3.6 | 3.6 |

The value in the table is an average of scores in the evaluation of five grades 1 to 5.

The creams obtained in Examples 8 to 10 showed excellent organoleptic properties in moist feeling and smoothness in comparison to the creams obtained in Comparative Examples 8 and 9.

EXAMPLE 11

Preparation of a Hair Care Product

| dimethyl 2,4-diethylglutarate | 1 g |
|---|---|
| polyoxyethylene (60) hardened castor oil | 1 g |
| ethanol | 70 g |
| purified water | 28 g |

(Method of Preparing a Hair Care Product)

(1) Dimethyl 2,4-diethylglutarate and polyoxyethylene (60) hardened castor oil were charged in a container, and heated at 60° C. to be uniformly dissolved.

(2) Ethanol was added to homogenize the solution.

(3) Purified water was added to homogenize the solution.

EXAMPLE 12

Preparation of a Hair Care Product

A hair care product was prepared in the same manner as in Example 11 except that dimethyl 2,4-diethylglutarate was replaced with dibutyl 2,4-diethylglutarate.

EXAMPLE 13

Preparation of a Hair Care Product

A hair care product was prepared in the same manner as in Example 11 except that dimethyl 2,4-diethylglutarate was replaced with di-2-ethylhexyl 2,4-diethylglutarate.

COMPARATIVE EXAMPLE 10

Preparation of a Hair Care Product

A hair care product was prepared in the same manner as in Example 11 except that dimethyl 2,4-diethylglutarate was replaced with di-2-ethylhexyl succinate.

TEST EXAMPLE 6

Organoleptic Evaluation of a Hair Care Product

Twenty man volunteers who were from 30 to 45 years old and divided into groups each consisting of five men used the hair care products prepared in Examples 11 to 13 and Comparative Example 10 twice a day for 1 week, and the organoleptic evaluation was performed. The evaluation was performed through score evaluation of five grades 1 to 5 (5: very good, 4: good, 3: average, 2: bad, 1: very bad) with respect to two items, a moist feeling and combing of the hair. The results are shown in Table 6.

TABLE 6

|  | Example 11 | Example 12 | Example 13 | Comparative Example 10 |
|---|---|---|---|---|
| Moist feeling | 4.4 | 4.2 | 4.8 | 4.0 |
| Combing | 4.6 | 4.2 | 4.0 | 3.6 |

The value in the table is an average of scores in the evaluation of five grades 1 to 5.

As shown in Table 6, the hair care products obtained in Examples 11 to 13 showed excellent organoleptic properties in moist feeling and combing in comparison to the hair care product obtained in Comparative Example 10.

INDUSTRIAL APPLICABILITY

The invention provides the oil for cosmetics comprising a dibasic acid diester which is excellent in solubility of the UV-A absorber and the like, the cosmetics comprising the oil for cosmetics thereof, and the like.

The invention claimed is:

1. An oil for cosmetics, comprising a dibasic acid diester represented by formula (I)

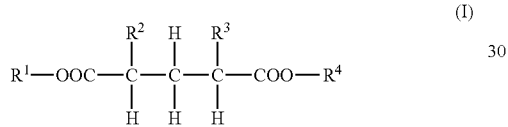

wherein $R^1$, $R^2$, $R^3$ and $R^4$, which are the same or different, each represent lower alkyl, lower alkenyl, lower alkynyl, cycloalkyl, aryl or aralkyl; and
   further comprising at least one ester-type oil selected from the group consisting of glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, glyceryl monostearate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, glyceryl tri(capryl·caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, stearyl 2-ethylhexanoate, cetostearyl 2-ethylhexanoate (mixture of cetyl 2-ethylhexanoate and stearyl 2-ethylhexanoate), glyceryl di-p-methoxycinnamic acid-mono-2-ethylhexanoate, hexyl isostearate, ethylene glycol dioctanoate, ethylene glycol dioleate, propylene glycol dicaprate, propylene glycol di-(capryl·caprate), propylene glycol dicaprylate, neopentylglycol dicaprate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isostearyl isostearate, octyldecyl isostearate, polyglycerol oleate, polyglycerol isostearate, triisocetyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyloxystearate, stearyl 12-stearoyloxystearate and isostearyl 12-stearoyloxystearate.

2. A cosmetic comprising:
   0.1 to 60 wt. % of a dibasic acid diester represented by formula (I)

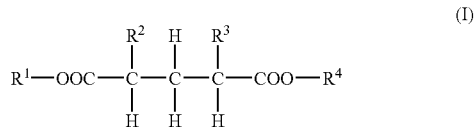

wherein $R^1$, $R^2$, $R^3$ and $R^4$, which are the same or different, each represent lower alkyl, lower alkenyl, lower alkynyl, cycloalkyl, aryl or aralkyl; and
   at least one member selected from the group consisting of a humectant, an emollient, a surfactant, an organic or inorganic pigment, an organic powder, a UV-B absorber, an antiseptic, a disinfectant, an antioxidant, a plant extract, a pH modifier, a perfume, an emulsion stabilizer and purified water.

3. A cosmetic according to claim 2, further comprising a UV-A absorber.

4. The cosmetics according to claim 3, wherein the UV-A absorber is 4-(tert-butyl)-4'-methoxydibenzoylmethane.

5. A dibasic acid diester represented by formula (Ia)

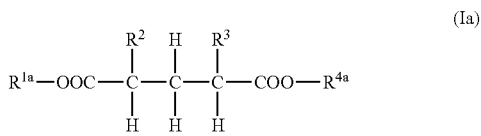

wherein $R^{1a}$, and $R^{4a}$, which are the same or different, each represent lower alkyl, lower alkenyl, lower alkynyl, cycloalkyl, aryl or aralkyl, provided that $R^{1a}$ and $R^{4a}$ are not ethyl at the same time; and
   $R^2$ and $R^3$ are both ethyl.

6. The cosmetic according to claim 3 further comprising at least one ester-type oil selected from the group consisting of glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, glyceryl monostearate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, glyceryl tri (capryl·caprate), trimethylpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, stearyl 2-ethylhexanoate, cetostearyl 2-ethylhexanoate (mixture of cetyl 2-ethylhexanoate and stearyl 2-ethylhexanoate), glyceryl di-p-methoxycinnamic acid-mono-2-ethylhexanoate, hexyl isostearate, ethylene glycol dioctanoate, ethylene glycol dioleate, propylene glycol dicaprate, propylene glycol di-(capryl·caprate), propylene glycol dicaprylate, neopentylglycol dicaprate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isostearyl isostearate, octyldecyl isostearate, polyglycerol oleate, polyglycerol isostearate, triisocetyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyloxystearate, stearyl 12-stearoyloxystearate and isostearyl 12-stearoyloxystearate.

7. The cosmetic according to claim 3 further comprising at least one hydrocarbon-type oil selected from the group consisting of squalane, liquid paraffin, α-olefin oligomer, isoparaffin, ceresine, paraffin, liquid isoparaffin, polybutene, microcrystalline wax and vaseline.

8. The cosmetic according to claim 3 further comprising at least one silicone-type oil selected from the group consisting of polymethylsilicone, methylphenylsilicone, methylcyclopolysiloxane, octamethylpolysiloxane, decamethylpolysiloxane, dodecamethylcyclosiloxane, a dimethylsiloxane.methylcetyloxysiloxane copolymer, a dimethylsiloxane.methylstearoyloxysiloxane copolymer, alkyl-modified silicone oil and amino-modified silicone oil.

9. The cosmetic according to claim 3 further comprising a pefflluoropolyether oil.

10. The cosmetic according to claim 3 further comprising at least one animal or plant oil selected from the group consisting of avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cotton seed oil, coconut oil, kukui nut oil, wheat embryo oil, rice embryo oil, shea butter, evening primrose oil, macadamia nut oil, meadow foam oil, yolk oil, tallow, horse oil, mink oil, orange roughy oil and jojoba oil.

11. An oil for cosmetics, comprising a dibasic acid diester represented by formula (I)

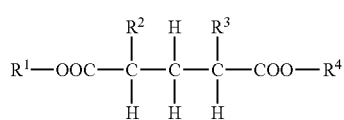

wherein $R^1$, $R^2$, $R^3$ and $R^4$, which are the same or different, each represent lower alkyl, lower alkenyl, lower alkynyl, cycloalkyl, aryl or aralkyl; and
    at least one hydrocarbon-type oil selected from the group consisting of squalane, liquid paraffin, α-olefin oligomer, isoparaffin, ceresine, paraffin, liquid isoparaffin, polybutene, microcrystalline wax and vaseline.

12. An oil for cosmetics, comprising a dibasic acid diester represented by formula (I)

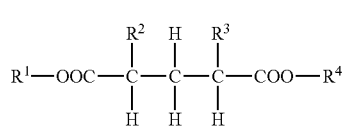

wherein $R^1$, $R^2$, $R^3$ and $R^4$, which are the same or different, each represent lower alkyl, lower alkenyl, lower alkynyl, cycloalkyl, aryl or aralkyl; and
    at least one silicone-type oil selected from the group consisting of polymethylsilicone, methylphenylsilicone, methylcyclopolysiloxane, octamethylpolysiloxane, decamethylpolysiloxane, dodecamethylcyclosiloxane, a dimethylsiloxane.methylcetyloxysiloxane copolymer, a dimethylsiloxane.methylstearoyloxysiloxane copolymer, alkyl-modified silicone oil and amino-modified silicone oil.

13. An oil for cosmetics, comprising a dibasic acid diester represented by formula (I)

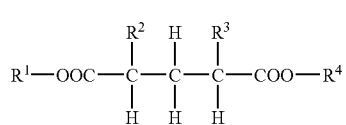

wherein $R^1$, $R^2$, $R^3$ and $R^4$, which are the same or different, each represent lower alkyl, lower alkenyl, lower alkynyl, cycloalkyl, aryl or aralkyl; and
    a perfluoropolyether oil.

14. An oil for cosmetics, comprising a dibasic acid diester represented by formula (I)

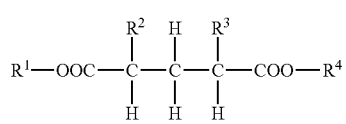

wherein $R^1$, $R^2$, $R^3$ and $R^4$, which are the same or different, each represent lower alkyl, lower alkenyl, lower alkynyl, cycloalkyl, aryl or aralkyl; and
    at least one animal or plant oil selected from the group consisting of avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cotton seed oil, coconut oil, kukui nut oil, wheat embryo oil, rice embryo oil, shea butter, evening primrose oil, macadamia nut oil, meadow foam oil, yolk oil, tallow, horse oil, mink oil, orange roughy oil and jojoba oil.

15. The cosmetic according to claim 3, wherein said UV-A absorber is contained at from 0.5 to 80 wt. %.

16. The cosmetic according to claim 4, wherein said UV-A absorber is contained at from 1 to 70 wt. %.

* * * * *

UNITED STATES PATENT AND TRADEMARK OFFICE
CERTIFICATE OF CORRECTION

| | | |
|---|---|---|
| PATENT NO. | : 7,417,162 B2 | Page 1 of 2 |
| APPLICATION NO. | : 10/487360 | |
| DATED | : August 26, 2008 | |
| INVENTOR(S) | : Yukitoshi Fukuda et al. | |

It is certified that error appears in the above-identified patent and that said Letters Patent is hereby corrected as shown below:

ON THE TITLE PAGE, ITEM (75) INVENTORS

"Tomoya Takahashi, Chiyoda-ku (JP)" should read --Tomoya Takahashi, Matsudo (JP)--.

ON THE TITLE PAGE, ITEM (56) FOREIGN PATENT DOCUMENTS

"07/14847" should read --07-14847--.

ON THE TITLE PAGE, ITEM (56), OTHER PUBLICATIONS

"Dinz-Colleja, et a.," should read --Dinz-Colleja, et al.,--.

COLUMN 2

Line 33, "lower-alkenyl" should read --lower alkenyl--; and
Line 52, "represented-by" should read --represented by--.

COLUMN 3

Line 48, "octyldecyl, isostearate," should read --octyldecyl isostearate,--.

COLUMN 6

Line 11, "WV-B" should read --UV-B--.

COLUMN 7

Line 44, "shows" should read --show--;
Line 57, "is" should read --are--; and
Line 60, "is" should read --are--.

COLUMN 8

Line 5, "is" should read --are--.

COLUMN 11

Line 49, "UV-A." should read --UV-A--.

UNITED STATES PATENT AND TRADEMARK OFFICE
CERTIFICATE OF CORRECTION

PATENT NO. : 7,417,162 B2
APPLICATION NO. : 10/487360
DATED : August 26, 2008
INVENTOR(S) : Yukitoshi Fukuda et al.

It is certified that error appears in the above-identified patent and that said Letters Patent is hereby corrected as shown below:

COLUMN 15

Line 65, "Ness" should read --ness--.

COLUMN 18

Line 33, "A" should read --The--; and
Line 35, "cosmetics" should read --cosmetic--.

COLUMN 19

Line 33, "dimethylsiloxane.m-" should read --dimethylsiloxane methyl- --;
Line 34, "ethylcetyloxysiloxane copolymer, a" should read --cetyloxysiloxane copolymer, a--; and
Line 38, "peffluoropolyether" should read --perfluoropolyether--.

Signed and Sealed this

Tenth Day of February, 2009

JOHN DOLL
*Acting Director of the United States Patent and Trademark Office*